United States Patent [19]
Fischer

[11] 3,976,468
[45] Aug. 24, 1976

[54] HERBICIDE MIXTURE OF LOWER ALKYL ESTERS OF N-BENZOYL-N-CHLOROPHENYL-2-AMINO-LOWER ALKANOIC ACIDS AND 3-LOWER ALKYL-2,1,3-BENZOTHIADIAZINONE-(4)-2,2-DIOXIDES OR SALTS THEREOF

[75] Inventor: Adolf Fischer, Mutterstadt, Germany

[73] Assignee: BASF Aktiengesellschaft, Ludwigshafen (Rhine), Germany

[22] Filed: July 10, 1974

[21] Appl. No.: 487,374

[30] Foreign Application Priority Data
July 18, 1973  Germany............................. 2336444

[52] U.S. Cl. .................................. 71/91; 71/105; 71/106; 71/108; 71/109; 71/110; 71/111; 71/116; 71/117; 71/121; 71/122
[51] Int. Cl.² ...................................... A01N 9/12
[58] Field of Search ................ 71/91, 106, 115, 111

[56] References Cited
UNITED STATES PATENTS

| | | | |
|---|---|---|---|
| 3,598,859 | 8/1971 | Yates et al. | 71/115 |
| 3,708,277 | 1/1973 | Zeidler et al. | 71/91 |
| 3,846,113 | 11/1974 | Fischer | 71/91 |

OTHER PUBLICATIONS
Fischer, "Herbicidal Compositions" (1971) CA 74 No. 110714w. (1971).

*Primary Examiner*—Glennon H. Hollrah
*Attorney, Agent, or Firm*—Johnston, Keil, Thompson & Shurtleff

[57] ABSTRACT

New and valuable herbicides containing mixtures, inter alia, of lower alkyl esters of N-benzoyl-N-chlorophenyl-2-amino-lower alkanoic acids and 3-lower alkyl-2,1,3-benzothiadiazinone-(4)-2,2-dioxides or salts thereof.

3 Claims, No Drawings

HERBICIDE MIXTURE OF LOWER ALKYL ESTERS OF N-BENZOYL-N-CHLOROPHENYL-2-AMINO-LOWER ALKANOIC ACIDS AND 3-LOWER ALKYL-2,1,3-BENZOTHIADIAZINONE-(4)-2,2-DIOXIDES OR SALTS THEREOF

The present invention relates to new and valuable herbicides containing compositions of different active ingredients.

It is known that benzoylaminocarboxylic acids, dinitrophenol derivatives, hydroxybenzonitriles, hydroxybenzaldoxime aryl ethers, benzothiadiazinone dioxides and phenoxycarboxylic acids have a herbicidal action. However, this action is not always satisfactory.

I have now found that a composition of
a. a compound of the formula

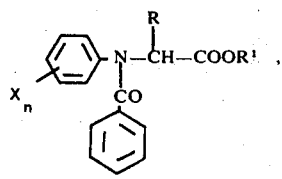

where X denotes halogen, alkyl, haloalkyl or alkoxy, R denotes hydrogen or lower alkyl, $R^1$ denotes lower alkyl, and n denotes one of the integers 0, 1, 2 and 3, and/or b. a compound of the formula

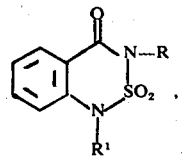

where R denotes lower alkyl, and $R^1$ denotes hydrogen, or a salt thereof, e.g. ammonium, potassium, sodium, lithium, calcium, magnesium, ethylamine, dimethylamine, diethylamine, diethanolamine, ethanolamine, dimethylethanolamine, trimethylamine salts, and/or c. a compound of the formula

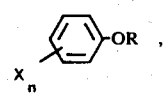

where X denotes chloro, bromo, nitro, iodo, cyano or lower alkyl, n denotes one of the integers 0, 1, 2 and 3, and R denotes hydrogen and salts thereof, e.g. sodium and lithium salts,

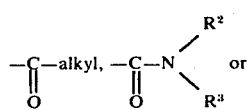

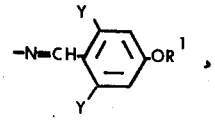

Y denoting chloro, iodo or bromo, $R^1$ denoting lower alkyl,

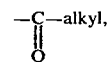

hydrogen and salts thereof, e.g., sodium salt, $R^2$ denoting hydrogen, lower alkyl or a substituted or unsubstituted aryl radical, and $R^3$ denoting hydrogen, lower alkyl or a substituted or unsubstituted aryl radical, and/or d. a compound of the formula

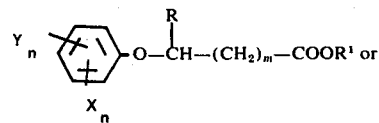

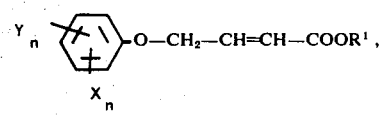

where X denotes chloro or methyl, Y denotes chloro or methyl, n denotes one of the integers 0, 1, 2 and 3, R denotes hydrogen or lower alkyl, m denotes one of the integers 0, 1 and 2 and $R^1$ denotes alkyl or hydrogen, or a salt thereof, e.g., sodium, potassium, dimethylamine, diethanolamine, and diethylamine salts, has a better herbicidal action than its constituents.

The compositions may contain one or more compounds of the formula a) and one of more compounds of the formulas b), c) or d).

The ratio of the active ingredients to each other is 1:0.1 to 10 parts by weight.

The amount used of the agents according to the invention may vary and depends in essence on the type of effect to be achieved; it is generally from 0.1 to 30 (and more), preferably 0.2 to 6, kg per hectare of active ingredient. The agents according to the invention may be used once or several times inter alia after planting, postemergence or during emergence of the crop or unwanted plants.

The compositions are selective in crops such as *Triticum spp.*, *Hordeum spp.*, *Secale spp.*, *Zea mays*, *Oryza sativa*, *Pisum sativum*, *Phaseolus vulgaris*, *Glycine max*, and *Solanum tuberosum*.

The compositions may also be used as total herbicides on ditches, aquatic areas, railroad tracks, and barren or waste land, etc.

Compositions of a+b, a+c, a+d, a+b+c, a+b+d, a+c+d, and b+c+d are preferred.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coaltar oils, etc. and oil of vegetable or mineral origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts or dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin,, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain 0.1 to 95, and preferably 0.5 to 90, % by weight of active ingredient.

There may be added to the compositions or individual active ingredients (if desired, immediately before use (tankmix) oils of various types, herbicides, fungicides, nematocides, insecticides, bactericides, trace elements, fertilizers, antifoams (e.g., silicones), growth regulators, antidotes and other herbicidally effective compounds such as substituted anilines substituted aryloxycarboxylic acids and salts, esters and amides thereof, substituted ethers
substituted arsonic acids and their salts, esters and amides
substituted benzimidazoles
substituted benzisothiazoles
substituted benzothiadiazinone dioxides
substituted benzoxazines
substituted benzoxazinones
substituted benzothiadiazoles
substituted biurets
substituted quinolines
substituted carbamates
substituted aliphatic carboxylic acids and their salts, esters and amides
substituted aromatic carboxylic acids and their salts, esters and amides
substituted carbamoylalkylthiol- or -dithiophosphates
substituted quinazolines
substituted cycloalkylamidocarbothiolic acids and their salts, esters and amides
substituted cycloalkylcarbonamidothiazoles
substituted dicarboxylic acids and their salts, esters and amides
substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substituted piperidines
substituted pyrazoles
substituted pyrazole alkylcarboxylic acids and their salts, esters and amides
substituted pyrazolium salts
substituted pyrazolium alkyl sulfates
substituted pyridazines substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the active ingredients or compositions thereof according to the invention.

These agents may be added to the herbicides according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance Gramineae, such as
Cynodon spp.
Digitaria spp.
Echinochloa spp.
Setaria spp.
Panicum spp.
Alopecurus spp.
Lolium spp.
Sorghum spp.
Agropyron spp.
Phalaris spp.
Apera spp.
etc.;
Cyperaceae, such as
Carex spp.
Cyperus spp.
etc.;
dicotyledonous weeds, such as
Malvaceae, e.g.,
Abutilon theoprasti
Sida spp.
etc.;
Compositae, such as
Ambrosia spp.
Lactuca spp.
Senecio spp.
Sonchus spp.
Xanthium spp.
Iva spp.
Galinsoga spp.
Taraxacum spp.
Chrysanthemum spp.
Cirsium spp.
Convolvulaceae, such as
Convolvulus spp.
Ipomoea spp.
etc.;
Cruciferae, such as
Barbarea vulgaris
Brassica spp.
Capsella spp.
Sisymbrium spp.
Thlaspi spp.
Sinapis arvensis
etc.;
Geraniaceae, such as
Erodium spp.
etc.;
Portulacaceae, such as
Portulaca spp.
Primulaceae, such is
Anagallis arvensis
etc.;
Rubiaceae, such as
Richardia spp.
Galium spp.
Scrophulariaceae, such as
Linaria spp.
Veronica spp.
Solanaceae, such as
Physalis spp.
Solanum spp.
etc.;
Urticaceae, such as
Urtica spp.
Violaceae, such as
Viola spp.
Zygophyllaceae, such as
Tribulus terrestis
Euphorbiaceae, such as
Mercurialis annua
Umbelliferae, such as
Daucus carota
Aethusa cynapium
Commelinaeae, such as
Commelina spp.
Labiatae, such as
Lamium spp.
etc.;
Leguminosae, such as
Medicago spp.
Trifolium spp.
Vicia spp.
etc.;
Plantaginaceae, such as
Plantago spp.
Polygonaceae, such as
Polygonum spp.
Rumex spp.
Aizoaceae, such as
Mollugo verticillata
Amaranthaceae, such as
Amaranthus spp.
Boraginaceae, such as
Amsinckia spp.
Myostis spp.
etc.;
Caryophyllaceae, such as
Stellaria spp.
Spergula spp.
Saponaria spp.
Scleranthus annuus
Chenopodiaceae, such as
Chenopodium spp.
Kochia spp.
Salsola Kali
Lythraceae, such as
Cuphea spp.
Oxalidaceae, such as
Oxalis spp.
Ranunculaceae, such as
Ranunculus spp.
Delphinium spp.
Papaveraceae, such as
Papaver spp.
etc.;
Onagraceae, such as Dactylis spp.
Avena spp.
Bromus spp.
Uniola spp.
Poa spp.
Leptochloa spp.
Brachiaria spp.
Eleusine spp.
Cenchrus spp.
Eragrostis spp.
Phragmitres communis Eleocharis spp.
Scirpus spp.

Hibiscus spp.
Malva spp.

Centaurea spp.
Tussilago spp.
Lapsana communis
Tagetes spp.
Erigeron spp.
Anthemis spp.
Matricaria spp.
Artemisia spp.
Bidens spp.
etc.;

Cuscuta spp.
Jaquemontia tamnifolia

Arabidopsis thaliana
Descurainia spp.
Draba spp.
Coronopus didymus
Lepidium spp.
Raphanus spp.

Geranium spp.

etc.;

Lysimachia spp.

Diodia spp.
etc.;

Digitalis spp.
etc.;

Nicandra spp.
Datura spp.

etc.;

etc.;

Euphorbia spp.

Ammi majus
etc.;

etc.;

Galeopsis spp.

Sesbania exaltata
Cassia spp.
Lathyrus spp.

etc.;

Fagopyrum spp.
etc.;

etc.;

etc.;

Anchusa spp.
Lithospermum spp.

Silene spp.
Cerastium spp.
Agrostemma githago
etc.;

Atriplex spp.
Monolepsis nuttalliana
etc.;

etc.;

Adonis spp.
etc.;

Fumaria officinalis

-continued

| | |
|---|---|
| *Jussiaea* spp. | etc.; |
| Rosaceae, such as | |
| *Alchemillia* spp. etc.; | *Potentilla* spp. |
| Potamogetonaceae, such as | |
| *Potamogeton* spp. | etc.; |
| Najadaceae, such as | |
| *Najas* spp. | etc.; |
| Equisetaceae | |
| *Equisetum* spp. | etc.; |
| Marsileaceae, such as | |
| *Marsilea quadrifolia* | etc.; |
| Polypodiaceae, | |
| *Pteridium quilinum* | |
| Alisamtaceae | |
| *Alisma* spp. etc. | *Sagittaria sagittifolia* |

In the greenhouse and in the open compositions of the following compounds were tested on the plants mentioned in the examples. The action of compositions of these compounds corresponds to that of the compositions in the examples:

3-methyl-2,1,3-benzothiadiazinone-(4)-2,2-dioxide
3-ethyl-2,1,3-benzothiadiazinone-(4)-2,2-dioxide
3-propyl-2,1,3-benzothiadiazinone-(4)-2,2-dioxide
3-butyl-2,1,3-benzothiadiazinone-(4)-2,2-dioxide
3-isobutyl-2,1,3-benzothiadiazinone-(4)-2,2-dioxide
3-isopropyl-2,1,3-benzothiadiazinone-(4)-2,2-dioxide
3-isopropyl-2,1,3-benzothiadiazinone-(4)-2,2-dioxide, sodium salt
3-isopropyl-2,1,3-benzothiadiazinone-(4)-2,2-dioxide, dimethylamine salt
3-isopropyl-2,1,3-benzothiadiazinone-(4)-2,2-dioxide, diethanolamine salt
3,5-dibromo-4-hydroxybenzaldoxime-O-(2',4'-dinitrophenyl)-ether
3,5-dibromo-4-hydroxybenzaldoxime-O-(2',4'-dinitrophenyl)-ether, sodium salt
3,5-dibromo-4-acetyloxybenzaldoxime-O-(2'-cyano-4'-nitrophenyl)-ether
3,5-dibromo-4-hydroxybenzaldoxime-O-(2'-cyano-4'-nitrophenyl)-ether
3,5-dibromo-4-hydroxybenzaldoxime-O-(2'-cyano-4'-cyanophenyl)-ether
3,5-dibromo-4-hydroxybenzaldoxime-O-(2'-cyano-4'-nitrophenyl)-ether, sodium salt
3,5-dibromo-4-propionyloxybenzaldoxime-O-(2'-cyano-4'-nitrophenyl)-ether
3,5-diiodo-4-hydroxybenzaldoxime-O-(2'-cyano-4'-nitrophenyl)-ether
3,5-diiodo-4-hydroxybenzaldoxime-O-(2'-cyano-4'-nitrophenyl)-ether, sodium salt
3,5-diiodo-4-hydroxybenzonitrile
3,5-diiodo-4-hydroxybenzonitrile, sodium salt
3,5-diiodo-4-hydroxybenzonitrile, lithium salt
3,5-dibromo-4-hydroxybenzonitrile
3,5-dibromo-4-hydroxybenzonitrile, sodium salt
3,5-dibromo-4-octanoyloxybenzonitrile
2-methyl-4,6-dinitrophenyl, sodium salt
2-sec-butyl-4,6-dinitrophenylacetate
2-tert-butyl-4,6-dinitrophenylacetate
2-tert-butyl-5-methyl-4,6-dinitrophenylacetate
2-isopropyl-3-methyl-4,6-dinitrophenol
2-sec-butyl-4,6-dinitrophenol, sodium salt
3,5-dibromo-4-phenylcarbamoyloxy-O-(2'-cyano-4'-nitrophenyl)-ether
3,5-dibromo-4-isopropylcarbamoyloxy-O-(2'-cyano-4'-nitrophenyl)-ether
3-isopropyl-2,1,3-benzothiadiazinone-(4)-2,2-dioxide, methylamine salt
3-isopropyl-2,1,3-benzothiadiazinone-(4)-2,2-dioxide, trimethylamine salt
3-isopropyl-2,1,3-benzothiadiazinone-(4)-2,2-dioxide, ethylamine salt
3-isopropyl-2,1,3-benzothiadiazinone-(4)-2,2-dioxide, diethylamine salt
3-isopropyl-2,1,3-benzothiadiazinone-(4)-2,2-dioxide, ethanolamine salt
3-isopropyl-2,1,3-benzothiadiazinone-(4)-2,2-dioxide, aniline salt
3-isopropyl-2,1,3-benzothiadiazinone-(4)-2,2-dioxide, pyridine salt
3-isopropyl-2,1,3-benzothiadiazinone-(4)-2,2-dioxide, phenylenediamine salt
3-isopropyl-2,1,3-benzothiadiazinone-(4)-2,2-dioxide, cyclohexylamine salt
3-isopropyl-2,1,3-benzothiadiazinone-(4)-2,2-dioxide, dodecylhexamethylenimine salt
3-isopropyl-2,1,3-benzothiadiazinone-(4)-2,2-dioxide, hydrazine salt
3-isopropyl-2,1,3-benzothiadiazinone-(4)-2,2-dioxide, magnesium salt
3-isopropyl-2,1,3-benzothiadiazinone-(4)-2,2-dioxide, calcium salt
3-isopropyl-2,1,3-benzothiadiazinone-(4)-2,2-dioxide, ammonium salt
3-isopropyl-2,1,3-benzothiadiazinone-(4)-2,2-dioxide, potassium salt
3-isopropyl-2,1,3-benzothiadiazinone-(4)-2,2-dioxide, lithium salt
3-isobutyl-2,1,3-benzothiadiazinone-(4)-2,2-dioxide sodium salt
3-isobutyl-2,1,3-benzothiadiazinone-(4)-2,2-dioxide dimethylamine salt
3-isobutyl-2,1,3-benzothiadiazinone-(4)-2,2-dioxide diethanolamine salt
3-sec-butyl-2,1,3-benzothiadiazinone-(4)-2,2-dioxide, sodium salt
3-sec-butyl-2,1,3-benzothiadiazinone-(4)-2,2-dioxide, dimethylamine salt
3-sec-butyl-2,1,3-benzothiadiazinone-(4)-2,2-dioxide, diethanolamine salt
3-n-butyl-2,1,3-benzothiadiazinone-(4)-2,2-dioxide, sodium salt
3-n-butyl-2,1,3-benzothiadiazinone-(4)-2,2-dioxide, dimethylamine salt
3-n-butyl-2,1,3-benzothiadiazinone-(4)-2,2-dioxide, diethanolamine salt
3-n-propyl-2,1,3-benzothiadiazinone-(4)-2,2-dioxide, sodium salt
3-n-propyl-2,1,3-benzothiadiazinone-(4)-2,2-dioxide, dimethylamine salt
3-n-propyl-2,1,3-benzothiadiazinone-(4)-2,2-dioxide, diethanolamine salt
3-ethyl-2,1,3-benzothiadiazinone-(4)-2,2-dioxide, sodium salt
3-ethyl-2,1,3-benzothiadiazinone-(4)-2,2-dioxide, dimethylamine salt
3-ethyl-2,1,3-benzothiadiazinone-(4)-2,2-dioxide, diethanolamine salt
3-methyl-2,1,3-benzothiadiazinone-(4)-2,2-dioxide, sodium salt
3-methyl-2,1,3-benzothiadiazinone-(4)-2,2-dioxide, dimethylamine salt
3-methyl-2,1,3-benzothiadiazinone-(4)-2,2-dioxide, diethanolamine salt 2-sec-amyl-4,6-dinitrophenol
2-(1-methylbutyl)-4,6-dinitrophenol
ethyl-N-benzoyl-N-(3,4-dichlorophenyl)-2-amino-propionate
α-(2,4-dichlorophenoxy)-propionic acid, dimethylamine salt
α-(2-methyl-4-chlorophenoxy)-propionic acid, dimethylamine salt
α-(2-methyl-4-chlorophenoxy)-propionic acid, sodium salt
α-(2-methylphenoxy)-propionic acid, dimethylamine salt
α-(2,4-dichlorophenoxy)-propionic acid, sodium salt
α(2,4,5-trichlorophenoxy)-propionic acid, potassium salt
α-(4-chlorophenoxy)-propionic acid, dimethylamine salt
isooctyl α-(2-methylphenoxy)-propionate
α-(2-methylphenoxy)-proponic acid, sodium salt
α(2-methyl-4-chlorophenoxy)-propionic acid, diethanolamine salt
α-(2-methyl-4-chlorophenoxy)-propionic acid, potassium salt
isooctyl α-(2,4-dichlorophenoxy)-propionate
amyl 2,4,5-trichlorophenoxyacetate
isooctyl 2,4,5-trichlorophenoxyacetate
2,4,5-trichlorophenoxyacetic acid, diethylamine salt
2,4-dichlorophenoxyacetic acid, dimethylamine salt
2-methyl-4-chlorophenoxyacetic acid, dimethylamine salt
2-methyl-4-chlorophenoxyacetic acid, sodium salt
2,4,5-trichlorophenoxyacetic acid, potassium salt
2,4,5-trichlorophenoxyacetic acid, dimethylamine salt
4-chlorophenoxyacetic acid, dimethylamine salt
2-chlorophenoxyacetic acid, dimethylamine salt
isooctyl 2-methyl-4-chlorophenoxyacetate
2,4-dichlorophenoxyacetic acid, sodium salt
isooctyl 2,4-dichlorophenoxyacetate
γ-(2,4-dichlorophenoxy)-butyric acid, dimethylamine salt
isooctyl γ-(2,4-dichlorophenoxy)-butyrate
γ-(2-methyl-4-chlorophenoxy)-butyric acid, sodium salt
γ-(2,4,5-trichlorophenoxy)-butyric acid, dimethylamine salt
γ-(4-chlorophenoxy)-butyric acid
γ-(2,4-dichlorophenoxy)-crotonic acid, dimethylamine salt

EXAMPLE 1

In the greenhouse, various plants were treated at a growth height of from 2 to 18 cm with the following amounts of the following individual active ingredients and compositions thereof as emulsions or oil dispersions:

I. ethyl-N-benzoyl-N-(3,4-dichlorophenyl)-2-aminopropionate, 0.5, 0.75, 1 and 1.5 kg/ha;
II. 3-isopropyl-2,1,3-benzothiadiazinone-(4)-2,2-dioxide, 0.5, 0.75, 1 and 1.5 kg/ha;
III. 3-isopropyl-2,1,3-benzothiadiazinone-(4)-2,2-dioxide, sodium salt 0.5, 0.75, 1 and 1.5 kg/ha;
IV. 3-isopropyl-2,1,3-benzothiadiazinone-(4)-2,2-dioxide, dimethylamine salt, 0.5, 0.75, 1 and 1.5 kg/ha;
V. 3-isopropyl-2,1,3-benzothiadiazinone-(4)-2,2-dioxide, diethanolamine salt, 0.5, 0.75, 1 and 1.5 kg/ha;
I+II: 0.5+1, 1+0.5 and 0.75+0.75 kg/ha;
I+III: 0.5+1, 1+0.5 and 0.75+0.75 kg/ha;
I+IV: 0.5+1, 1+0.5 and 0.75+0.75 kg/ha;
I+V: 0.5+1, 1+0.5 and 0.75+0.75 kg/ha.

After 14 to 18 days it was ascertained that the compositions had a better herbicidal action than their components, combined with the same good crop plant compatibility.

The results are give below:

| Active ingredient kg/ha | I | | | | II | | | | III | | | |
|---|---|---|---|---|---|---|---|---|---|---|---|---|
| | 0.5 | 0.75 | 1 | 1.5 | 0.5 | 0.75 | 1 | 1.5 | 0.5 | 0.75 | 1 | 1.5 |
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Avena fatua | 25 | 37 | 45 | 60 | 0 | 0 | 0 | 0 | 0 | 0 | 0 | 0 |
| Galium aparine | 0 | 6 | 10 | 14 | 35 | 45 | 60 | 75 | 30 | 40 | 60 | 75 |
| Stellaria media | 7 | 10 | 12 | 15 | 30 | 40 | 60 | 70 | 20 | 30 | 55 | 70 |

| Active ingredient | IV | | | | V | | | |
|---|---|---|---|---|---|---|---|---|
| Triticum aestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Avena fatua | 0 | 0 | 0 | 0 | 0 | 0 | 0 | 0 |
| Galium aparine | 30 | 40 | 50 | 60 | 35 | 45 | 65 | 80 |
| Stellaria media | 20 | 35 | 50 | 70 | 20 | 40 | 60 | 85 |

0 = no damage
100 = complete destruction

| Active ingredient kg/ha | I+II | | | I+III | | |
|---|---|---|---|---|---|---|
| | 0.5+1 | 1+0.5 | 0.75+0.75 | 0.5+1 | 1+0.5 | 0.75+0.75 |
| Triticum aestivum | 0 | 0 | 0 | 0 | 0 | 0 |
| Hordeum vulgare | 0 | 0 | 0 | 0 | 0 | 0 |
| Secale cereale | 0 | 0 | 0 | 0 | 0 | 0 |
| Avena fatua | 67 | 90 | 75 | 65 | 87 | 73 |
| Galium aparine | 95 | 92 | 90 | 97 | 80 | 85 |
| Stellaria media | 100 | 80 | 93 | 96 | 75 | 80 |

| Active ingredient | I+IV | | | I+V | | |
|---|---|---|---|---|---|---|
| Triticum aestivum | 0 | 0 | 0 | 0 | 0 | 0 |
| Hordeum vulgare | 0 | 0 | 0 | 0 | 0 | 0 |

| | | | | | | |
|---|---|---|---|---|---|---|
| Secale cereale | 0 | 0 | 0 | 0 | 0 | 0 |
| Avena fatua | 70 | 92 | 78 | 68 | 90 | 80 |
| Galium aparine | 94 | 85 | 90 | 97 | 87 | 95 |
| Stellaria media | 98 | 78 | 86 | 100 | 80 | 90 |

0 = no damage
100 = complete destruction

EXAMPLE 2

In the greenhouse, various plants were treated at a growth height of from 3 to 25 cm with the following amounts of the following individual active ingredients and compositions thereof as dispersions:

I. ethyl-N-benzoyl-N-(3,4-dichlorophenyl)-2-aminopropionate, 0.5, 1.5, 2.5 and 3 kg/ha;
II. 3-isopropyl-2,1,3-benzothiadiazinone-(4)-2,2-dioxide, 0.5, 1.5, 2.5 and 3 kg/ha;
III. 3-isopropyl-2,1,3-benzothiadiazinone-(4)-2,2-dioxide, sodium salt, 0.5, 1.5, 2.5 and 3 kg/ha;
IV. 3-isopropyl-2,1,3-benzothiadiazinone-(4)-2,2-dioxide, dimethylamine salt, 0.5, 1.5, 2.5 and 3 kg/ha;
V. 3-isopropyl-2,1,3-benzothiadiazinone-(4)-2,2-dioxide, diethanolamine salt, 0.5, 1.5, 2.5 and 3 kg/ha;
I+II: 2.5+0.5, 0.5+2.5 and 1.5+1.5 kg/ha;
I+III: 2.5+0.5, 0.5+2.5 and 1.5+1.5 kg/ha;
I+IV 2.5+0.5, 0.5+2.5 and 1.5+1.5 kg/ha;
I+V: 2.5+0.5, 0.5+2.5 and 1.5+1.5 kg/ha;

After 15 to 18 days it was ascertained that the compositions had a better herbicidal action than their components, combined with the same good crop plant compatibility.

The results are given below:

EXAMPLE 3

In the greenhouse, various plants were treated at a growth height of from 2 to 20 cm with the following amounts of the following individual active ingredients and compositions thereof as pastes:

I. ethyl-N-benzoyl-N-(3,4-dichlorophenyl)-2-aminopropionate, 0.25, 1 and 1.5 kg/ha;
IV. 3-isopropyl-2,1,3-benzothiadiazinone-(4)-2,2-dioxide, dimethylamine salt, 0.25, 1 and 1.5 kg/ha;
VI. 2-sec-butyl-4,6-dinitrophenyl acetate, 0.25, 1 and 1.5 kg/ha;
VII. 3,5-diiodo-4-hydroxybenzonitrile, lithium salt, 0.25, 1 and 1.5 kg/ha;
VIII. 3,5-dibromo-4-hydroxybenzaldoxime-O-(2',4'-dinitrophenyl)-ether, sodium salt, 0.25, 1 and 1.5 kg/ha;
IX. 3,5-dibromo-4-hydroxybenzaldoxime-O-(2'-cyano-4'-nitrophenyl)-ether, sodium salt, 0.25, 1 and 1.5 kg/ha;
I+IV+VII: 1+0.25+0.25, 0.25+1+0.25 and 0.25+0.25+1 kg/ha;
I+IV+VIII: 1+0.25+0.25, 0.25+1+0.25 and 0.25+0.25+1 kg/ha;
I+IV+IX: 1+0.25+0.25, 0.25+1+0.25 and 0.25+0.25+1 kg/ha;
I+IV+VI: 1+0.25+0.25, 0.25+1+0.25 and 0.25+0.25+1 kg/ha.

| Active ingredient | I | | | | II | | | | III | | | |
|---|---|---|---|---|---|---|---|---|---|---|---|---|
| kg/ha | 0.5 | 1.5 | 2.5 | 3 | 0.5 | 1.5 | 2.5 | 3 | 0.5 | 1.5 | 2.5 | 3 |
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Avena fatua | 25 | 60 | 78 | 95 | 0 | 0 | 0 | 0 | 0 | 0 | 0 | 0 |
| Galium aparine | 0 | 14 | 23 | 35 | 35 | 75 | 90 | 95 | 30 | 75 | 90 | 95 |
| Stellaria media | 7 | 15 | 20 | 29 | 30 | 70 | 86 | 95 | 20 | 70 | 90 | 94 |

| Active ingredient | IV | | | | V | | | |
|---|---|---|---|---|---|---|---|---|
| Triticum aestivum | 0 | 0 | 0 | 0 | 0 | 0 | 0 | 0 |
| Hordeum vulgare | 0 | 0 | 0 | 0 | 0 | 0 | 0 | 0 |
| Secale cereale | 0 | 0 | 0 | 0 | 0 | 0 | 0 | 0 |
| Avena fatua | 0 | 0 | 0 | 0 | 0 | 0 | 0 | 0 |
| Galium aparine | 30 | 60 | 90 | 100 | 35 | 80 | 90 | 95 |
| Stellaria media | 20 | 70 | 93 | 95 | 20 | 85 | 100 | 100 |

0 = no damage
100 = complete destruction

| Active ingredient kg/ha | I+II | | | I+III | | | I+IV | | | I+V | | |
|---|---|---|---|---|---|---|---|---|---|---|---|---|
| | 2.5+0.5 | 1.5+1.5 | 0.5+2.5 | 2.5+0.5 | 1.5+1.5 | 0.5+2.5 | 2.5+0.5 | 1.5+1.5 | 0.5+2.5 | 2.5+0.5 | 1.5+1.5 | 0.5+2.5 |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Avena fatua | 100 | 96 | 70 | 100 | 95 | 72 | 100 | 97 | 70 | 100 | 95 | 68 |
| Galium aparine | 97 | 100 | 100 | 98 | 100 | 100 | 96 | 100 | 100 | 100 | 100 | 100 |
| Stellaria media | 96 | 100 | 100 | 90 | 100 | 100 | 87 | 100 | 100 | 90 | 100 | 100 |

0 = no damage
100 = complete destruction

After 12 to 14 days it was ascertained that the compositions had a better herbicidal action than their components, combined with the same good crop plant compatibility.

The results are given below:

| Active ingredient kg/ha | I | | | IV | | | VI | | | VII | | |
|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 |
| Crop plants: | | | | | | | | | | | | |
| Triticum aestivum | 0 | 0 | 0 | 0 | 0 | 0 | 0 | 0 | 0 | 0 | 10 | 20 |
| Hordeum vulgare | 0 | 0 | 0 | 0 | 0 | 0 | 0 | 0 | 0 | 0 | 10 | 10 |
| Secale cereale | 0 | 0 | 0 | 0 | 0 | 0 | 0 | 0 | 0 | 0 | 20 | 20 |
| Unwanted plants: | | | | | | | | | | | | |
| Avena fatua | 10 | 45 | 60 | 0 | 0 | 0 | 0 | 10 | 15 | 0 | 0 | 0 |
| Galium aparine | 0 | 10 | 14 | 20 | 50 | 60 | 18 | 40 | 50 | 15 | 60 | 70 |
| Stellaria media | 5 | 12 | 15 | 25 | 50 | 75 | 20 | 60 | 75 | 25 | 55 | 80 |

| Active ingredient | VIII | | | IX | | |
|---|---|---|---|---|---|---|
| Triticum aestivum | 0 | 0 | 10 | 0 | 0 | 0 |
| Hordeum vulgare | 0 | 0 | 15 | 0 | 0 | 0 |
| Secale cereale | 0 | 0 | 15 | 0 | 0 | 5 |
| Avena fatua | 0 | 0 | 0 | 0 | 0 | 0 |
| Galium aparine | 20 | 50 | 60 | 25 | 95 | 100 |
| Stellaria media | 15 | 48 | 70 | 20 | 80 | 100 |

0 = no damage
100 = complete destruction

| Active ingredient kg/ha | I+IV+VI | | | I+IV+VII | | |
|---|---|---|---|---|---|---|
| | 1+0.25+0.25 | 0.25+1+0.25 | 0.25+0.25+1 | 1+0.25+0.25 | 0.25+1+0.25 | 0.25+0.25+1 |
| Triticum aestivum | 0 | 0 | 0 | 0 | 0 | 10 |
| Hordeum vulgare | 0 | 0 | 0 | 0 | 0 | 10 |
| Secale cereale | 0 | 0 | 0 | 0 | 0 | 20 |
| Avena fatua | 87 | 58 | 60 | 80 | 54 | 57 |
| Galium aparine | 90 | 95 | 90 | 87 | 97 | 90 |
| Stellaria media | 95 | 92 | 100 | 98 | 100 | 100 |

| Active ingredient | I+IV+VIII | | | I+IV+IX | | |
|---|---|---|---|---|---|---|
| Triticum aestivum | 0 | 0 | 0 | 0 | 0 | 0 |
| Hordeum vulgare | 0 | 0 | 0 | 0 | 0 | 0 |
| Secale cereale | 0 | 0 | 0 | 0 | 0 | 0 |
| Avena fatua | 90 | 62 | 65 | 92 | 60 | 64 |
| Galium aparine | 93 | 100 | 100 | 98 | 100 | 100 |
| Stellaria media | 95 | 100 | 100 | 100 | 100 | 100 |

0 = no damage
100 = complete destruction

EXAMPLE 4

In the open, various plants were treated at a growth height of from 2 to 24 cm with the following amounts of the following individual active ingredients and compositions thereof as tankmix emulsions or dispersions:

I. ethyl-N-benzoyl-N-(3,4-dichlorophenyl)-2-aminopropionate, 0.25, 1 and 1.5 kg/ha;
II. 3-isopropyl-2,1,3-benzothiadiazinon-(4)-2,2-dioxide, 0.25, 1 and 1.5 kg/ha;
III. 3-isopropyl-2,1,3-benzothiadiazinone-(4)-2,2-dioxide, sodium salt, 0.25, 1 and 1.5 kg/ha;
IV. 3-isopropyl-2,1,3-benzothiadiazinone-(4)-2,2-dioxide, dimethylamine salt, 0.25, 1 and 1.5 kg/ha;
V. 3-isopropyl-2,1,3-benzothiadiazinone-(4)-2,2-dioxide, diethanolamine salt, 0.25, 1 and 1.5 kg/ha;
VI. 2-sec-butyl-4,6-dinitrophenyl acetate, 0.25, 1 and 1.5 kg/ha;
VII. 3,5-diiodo-4-hydroxybenzonitrile, lithium salt, 0.25, 1 and 1.5 kg/ha;
VIII. 3,5-dibromo-4-hydroxybenzaldoxime-O-(2',4'-dinitrophenyl)-ether, sodium salt, 0.25, 1 and 1.5 kg/ha;
IX. 3,5-dibromo-4-hydroxybenzaldoxime-O-(2'-cyano-4'-nitrophenyl)-ether, sodium salt, 0.25, 1 and 1.5 kg/ha;
X. 3,5-dibromo-4-hydroxybenzonitrile, sodium salt, 0.25, 1 and 1.5 kg/ha;
XI. α-(2-methyl-4-chlorophenoxy)-propionic acid, dimethylamine salt, 0.25, 1 and 1.5 kg/ha;
XII. α-(2,4-dichlorophenoxy)-propionic acid, dimethylamine salt, 0.25, 1 and 1.5 kg/ha;
XIII. 2,4-dichlorophenoxyacetic acid, dimethylamine salt, 0.25, 1 and 1.5 kg/ha;
XIV. 2-methyl-4-chlorophenoxyacetic acid, dimethylamine salt, 0.25, 1 and 1.5 kg/ha;
XV. α-(2,4,5-trichlorophenoxy)-propionic acid, dimethylamine salt, 0.25, 1 and 1.5 kg/ha;
XVI. 2,4,5-trichlorophenoxyacetic acid, potassium salt, 0.25, 1 and 1.5 kg/ha;
XVII. γ-(2,4-dichlorophenoxy)-butyric acid, dimethylamine salt, 0.25, 1 and 1.5 kg/ha;

I+II+VI, I+II+VII, I+II+VIII, I+II+IX, I+II+X, I+III+VI, I+III+VII,
I+III+VIII, I+III+IX, I+III+X, I+V+VI, I+V+VII, I+V+VIII, I+V+IX,
I+V+X, I+IV+X, I+II+IX, I+II+XII, I+II+XIII, I+II+XIV, I+II+XV,
I+II+XVI, I+III+XI, I+III+XII, I+III+XIII, I+III+XIV, I+III+XV,
I+III+XVI, I+IV+XI, I+IV+XII, I+IV+XIII, I+IV+XIV, I+IV+XV, I+IV+XVI,
I+V+XI, I+V+XII, I+V+XIII, I+V+XIV, I+V+XV, I+V+XVI, I+VI+XI,
I+VI+XII, I+VI+XIII, I+VI+XIV, I+VI+XV, I+ VI+XVI, I+VII+XI, I+VII+XII,
I+VII+XIII, I+VII+XIV, I+VII+XV, I+VII+XVI, I+VIII+XI, I+VIII+XII,

I+VIII+XIII, I+VIII+XIV, I+VIII+XV, I+VIII+XVI, I+IX+XI, I+IX+XII,
I+IX+XIII, I+IX+XIV, I+IX+XV, I+IX+XVI, I+X+XI, I+X+XII, I+X+XIII,
I+X+XIV, I+X+XV, I+X+XVI, I+XVI+XI, I+XVI+XII, I+XVI+XIII, I+XVI+XIV,
I+XIII+XI, I+XIII+XIV, I+II+XVII, I+III+XVII, I+IV+XII, I+V+XVII,
I+VI+XVII, I+VII+XVII, I+VIII+XVII, I+IX+XVII, I+X+XVII, each of the above compositions at rates of 1+0.25+0.25, 0.25+1+0.25 and 0.25+0.25+1 kg/ha.

After 12 to 14 days it was ascertained that the compositions had a better herbicidal action than their components, combined with the same good crop plant compatibility.

The results are given below.

| Active ingredient kg/ha | I | | | II | | | III | | | IV | | |
|---|---|---|---|---|---|---|---|---|---|---|---|---|
| | 0.25 | 1 | 1.5 | 0.25 | 1 | 1.5 | 0.25 | 1 | 1.5 | 0.25 | 1 | 1.5 |
| Crop plants: | | | | | | | | | | | | |
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Unwanted plants: | | | | | | | | | | | | |
| Avena fatua | 10 | 45 | 60 | 0 | 0 | 0 | 0 | 0 | 0 | 0 | 0 | 0 |
| Galium aparine | 0 | 10 | 14 | 15 | 60 | 75 | 15 | 60 | 75 | 20 | 50 | 60 |
| Stellaria media | 5 | 12 | 15 | 25 | 60 | 70 | 10 | 55 | 70 | 25 | 50 | 70 |

| Active ingredient | V | | | VI | | | VII | | | VIII | | |
|---|---|---|---|---|---|---|---|---|---|---|---|---|
| Triticum aestivum | 0 | 0 | 0 | 0 | 0 | 0 | 0 | 10 | 20 | 0 | 0 | 10 |
| Hordeum vulgare | 0 | 0 | 0 | 0 | 0 | 0 | 0 | 10 | 10 | 0 | 0 | 15 |
| Secale cereale | 0 | 0 | 0 | 0 | 0 | 5 | 0 | 20 | 20 | 0 | 0 | 10 |
| Avena fatua | 0 | 0 | 0 | 0 | 10 | 15 | 0 | 0 | 0 | 0 | 0 | 0 |
| Galium aparine | 25 | 65 | 80 | 18 | 40 | 50 | 15 | 60 | 70 | 20 | 50 | 60 |
| Stellaria media | 10 | 60 | 85 | 20 | 60 | 75 | 25 | 55 | 80 | 15 | 48 | 70 |

| Active ingredient | IX | | | X | | | XI | | | XII | | |
|---|---|---|---|---|---|---|---|---|---|---|---|---|
| Triticum aestivum | 0 | 0 | 0 | 0 | 10 | 12 | 0 | 0 | 0 | 0 | 0 | 0 |
| Hordeum vulgare | 0 | 0 | 0 | 0 | 5 | 6 | 0 | 0 | 0 | 0 | 0 | 0 |
| Secale cereale | 0 | 0 | 5 | 0 | 8 | 10 | 0 | 0 | 0 | 0 | 0 | 0 |
| Avena fatua | 0 | 0 | 0 | 0 | 0 | 0 | 0 | 0 | 0 | 0 | 0 | 5 |
| Galium aparine | 25 | 90 | 100 | 10 | 50 | 67 | 15 | 50 | 70 | 10 | 65 | 75 |
| Stellaria media | 20 | 80 | 100 | 15 | 54 | 78 | 20 | 45 | 70 | 15 | 55 | 75 |

| Active ingredient | XIII | | | XIV | | | XV | | | XVI | | |
|---|---|---|---|---|---|---|---|---|---|---|---|---|
| Triticum aestivum | 0 | 0 | 0 | 0 | 0 | 0 | 0 | 5 | 10 | 0 | 0 | 0 |
| Hordeum vulgare | 0 | 0 | 0 | 0 | 0 | 0 | 0 | 7 | 10 | 0 | 0 | 5 |
| Secale cereale | 0 | 0 | 0 | 0 | 0 | 0 | 0 | 10 | 12 | 0 | 0 | 7 |
| Avena fatua | 0 | 0 | 0 | 0 | 0 | 0 | 0 | 4 | 10 | 0 | 0 | 0 |
| Galium aparine | 5 | 20 | 25 | 5 | 20 | 25 | 20 | 60 | 85 | 15 | 60 | 80 |
| Stellaria media | 3 | 10 | 20 | 10 | 20 | 35 | 15 | 65 | 85 | 5 | 20 | 36 |

| Active ingredient | XVII | | |
|---|---|---|---|
| Triticum aestivum | 0 | 0 | 0 |
| Hordeum vulgare | 0 | 0 | 0 |
| Secale cereale | 0 | 0 | 0 |
| Avena fatua | 0 | 0 | 0 |
| Galium aparine | 9 | 18 | 25 |
| Stellaria media | 2 | 8 | 15 |

| Active ingredient kg/ha | I+II+VI | | | I+II+VII | | | I+II+VIII | | |
|---|---|---|---|---|---|---|---|---|---|
| | 1+0.25+0.25 | 0.25+1+0.25 | 0.25+0.25+1 | 1+0.25+0.25 | 0.25+1+0.25 | 0.25+0.25+1 | 1+0.25+0.25 | 0.25+1+0.25 | 0.25+0.25+1 |
| Triticum aestivum | 0 | 0 | 0 | 0 | 0 | 10 | 0 | 0 | 0 |
| Hordeum vulgare | 0 | 0 | 0 | 0 | 0 | 10 | 0 | 0 | 0 |
| Secale cereale | 0 | 0 | 0 | 0 | 0 | 20 | 0 | 0 | 0 |
| Avena fatua | 90 | 56 | 65 | 80 | 50 | 52 | 77 | 48 | 50 |
| Galium aparine | 85 | 100 | 98 | 84 | 100 | 100 | 90 | 100 | 100 |
| Stellaria media | 90 | 100 | 100 | 100 | 100 | 100 | 96 | 100 | 100 |

| Active ingredient | I+II+IX | | | I+II+X | | | I+III+VI | | |
|---|---|---|---|---|---|---|---|---|---|
| Triticum aestivum | 0 | 0 | 0 | 0 | 0 | 10 | 0 | 0 | 0 |
| Hordeum vulgare | 0 | 0 | 0 | 0 | 0 | 5 | 0 | 0 | 0 |
| Secale cereale | 0 | 0 | 0 | 0 | 0 | 8 | 0 | 0 | 0 |
| Avena fatua | 80 | 52 | 54 | 75 | 49 | 50 | 90 | 55 | 64 |
| Galium aparine | 87 | 100 | 100 | 78 | 98 | 100 | 75 | 100 | 93 |
| Stellaria media | 100 | 100 | 100 | 90 | 100 | 100 | 80 | 100 | 97 |

| Active ingredient | I+III+VII | | | I+III+VIII | | | I+III+IX | | |
|---|---|---|---|---|---|---|---|---|---|
| Triticum aestivum | 0 | 0 | 10 | 0 | 0 | 0 | 0 | 0 | 0 |
| Hordeum vulgare | 0 | 0 | 10 | 0 | 0 | 0 | 0 | 0 | 0 |
| Secale cereale | 0 | 0 | 20 | 0 | 0 | 0 | 0 | 0 | 0 |
| Avena fatua | 82 | 50 | 53 | 82 | 54 | 57 | 80 | 52 | 54 |
| Galium aparine | 80 | 100 | 100 | 84 | 100 | 98 | 85 | 100 | 100 |
| Stellaria media | 98 | 100 | 100 | 75 | 100 | 95 | 80 | 100 | 100 |

| Active ingredient | I+III+X | | | I+V+VI | | | I+V+VII | | |
|---|---|---|---|---|---|---|---|---|---|
| Triticum aestivum | 0 | 0 | 10 | 0 | 0 | 0 | 0 | 0 | 10 |
| Hordeum vulgare | 0 | 0 | 5 | 0 | 0 | 0 | 0 | 0 | 10 |

-continued

| | | | | | | | | | |
|---|---|---|---|---|---|---|---|---|---|
| Secale cereale | 0 | 0 | 8 | 0 | 0 | 0 | 0 | 0 | 20 |
| Avena fatua | 76 | 48 | 50 | 83 | 53 | 66 | 80 | 48 | 50 |
| Galium aparine | 74 | 100 | 98 | 92 | 100 | 97 | 90 | 100 | 100 |
| Stellaria media | 80 | 100 | 100 | 85 | 100 | 100 | 88 | 100 | 97 |
| Active ingredient | I+V+VIII | | | I+V+IX | | | I+V+X | | |
| Triticum aestivum | 0 | 0 | 0 | 0 | 0 | 0 | 0 | 0 | 10 |
| Hordeum vulgare | 0 | 0 | 0 | 0 | 0 | 0 | 0 | 0 | 5 |
| Secale cereale | 0 | 0 | 0 | 0 | 0 | 0 | 0 | 0 | 8 |
| Avena fatua | 90 | 55 | 60 | 88 | 53 | 58 | 80 | 47 | 48 |
| Galium aparine | 92 | 100 | 100 | 100 | 100 | 100 | 87 | 100 | 100 |
| Stellaria media | 82 | 100 | 98 | 86 | 100 | 100 | 83 | 100 | 98 |
| Active ingredient | I+IV+X | | | I+II+XI | | | I+II+XII | | |
| Triticum aestivum | 0 | 0 | 10 | 0 | 0 | 0 | 0 | 0 | 0 |
| Hordeum vulgare | 0 | 0 | 5 | 0 | 0 | 0 | 0 | 0 | 0 |
| Secale cereale | 0 | 0 | 8 | 0 | 0 | 0 | 0 | 0 | 0 |
| Avena fatua | 82 | 50 | 50 | 83 | 49 | 48 | 86 | 52 | 56 |
| Galium aparine | 80 | 95 | 100 | 84 | 100 | 94 | 76 | 100 | 100 |
| Stellaria media | 90 | 100 | 100 | 100 | 100 | 100 | 90 | 100 | 100 |
| Active ingredient | I+II+XIII | | | I+II+XIV | | | I+II+XV | | |
| Triticum aestivum | 0 | 0 | 0 | 0 | 0 | 0 | 0 | 0 | 5 |
| Hordeum vulgare | 0 | 0 | 0 | 0 | 0 | 0 | 0 | 0 | 7 |
| Secale cereale | 0 | 0 | 0 | 0 | 0 | 0 | 0 | 0 | 10 |
| Avena fatua | 82 | 48 | 47 | 80 | 49 | 50 | 85 | 53 | 55 |
| Galium aparine | 73 | 93 | 77 | 72 | 98 | 75 | 96 | 100 | 100 |
| Stellaria media | 80 | 96 | 82 | 90 | 100 | 88 | 90 | 100 | 100 |
| Active ingredient | I+II+XVI | | | I+III+XI | | | I+III+XII | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 80 | 47 | 49 | 82 | 49 | 51 | 86 | 52 | 54 |
| Galium aparine | 88 | 100 | 100 | 83 | 100 | 94 | 77 | 100 | 100 |
| Stellaria media | 80 | 100 | 88 | 80 | 100 | 96 | 80 | 100 | 100 |
| Active ingredient | I+III+XIII | | | I+III+XIV | | | I+III+XV | | |
| Triticum aestivum | 0 | 0 | 0 | 0 | 0 | 0 | 0 | 0 | 5 |
| Hordeum vulgare | 0 | 0 | 0 | 0 | 0 | 0 | 0 | 0 | 7 |
| Secale cereale | 0 | 0 | 0 | 0 | 0 | 0 | 0 | 0 | 10 |
| Avena fatua | 81 | 50 | 49 | 83 | 50 | 49 | 84 | 52 | 54 |
| Galium aparine | 73 | 97 | 75 | 74 | 95 | 77 | 90 | 100 | 100 |
| Stellaria media | 68 | 96 | 70 | 75 | 100 | 76 | 82 | 100 | 100 |
| Active ingredient | I+III+XVI | | | I+IV+XI | | | I+IV+XII | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 80 | 47 | 49 | 87 | 50 | 55 | 92 | 56 | 55 |
| Galium aparine | 83 | 100 | 100 | 90 | 96 | 100 | 78 | 97 | 100 |
| Stellaria media | 70 | 95 | 76 | 94 | 100 | 100 | 90 | 100 | 100 |
| Active ingredient | I+IV+XIII | | | I+IV+XIV | | | I+IV+XV | | |
| Triticum aestivum | 0 | 0 | 0 | 0 | 0 | 0 | 0 | 0 | 5 |
| Hordeum vulgare | 0 | 0 | 0 | 0 | 0 | 0 | 0 | 0 | 7 |
| Secale cereale | 0 | 0 | 0 | 0 | 0 | 0 | 0 | 0 | 10 |
| Avena fatua | 78 | 48 | 47 | 80 | 47 | 49 | 85 | 50 | 60 |
| Galium aparine | 75 | 90 | 75 | 72 | 92 | 80 | 87 | 100 | 100 |
| Stellaria media | 78 | 100 | 82 | 85 | 97 | 93 | 90 | 100 | 100 |
| Active ingredient | I+IV+XVI | | | I+V+XI | | | I+V+XII | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 80 | 47 | 49 | 83 | 52 | 50 | 85 | 60 | 60 |
| Galium aparine | 84 | 100 | 100 | 86 | 100 | 100 | 85 | 100 | 100 |
| Stellaria media | 80 | 98 | 87 | 84 | 100 | 97 | 86 | 100 | 100 |
| Active ingredient | I+V+XIII | | | I+V+XIV | | | I+V+XV | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 85 | 50 | 48 | 85 | 52 | 50 | 85 | 54 | 52 |
| Galium aparine | 83 | 100 | 85 | 82 | 100 | 85 | 95 | 100 | 100 |
| Stellaria media | 75 | 100 | 70 | 80 | 100 | 80 | 85 | 100 | 100 |
| Active ingredient | I+V+XVI | | | I+VI+XI | | | I+VI+XII | | |
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 85 | 50 | 48 | 85 | 52 | 54 | 85 | 55 | 56 |
| Galium aparine | 90 | 100 | 100 | 83 | 95 | 100 | 78 | 90 | 100 |
| Stellaria media | 76 | 100 | 82 | 92 | 100 | 100 | 87 | 100 | 100 |

-continued

| Active ingredient | I+VI+XIII | | | I+VI+XIV | | | I+VI+XV | | |
|---|---|---|---|---|---|---|---|---|---|
| Triticum aestivum | 0 | 0 | 0 | 0 | 0 | 0 | 0 | 0 | 5 |
| Hordeum vulgare | 0 | 0 | 0 | 0 | 0 | 0 | 0 | 0 | 7 |
| Secale cereale | 0 | 0 | 0 | 0 | 0 | 0 | 0 | 0 | 10 |
| Avena fatua | 82 | 68 | 46 | 80 | 60 | 49 | 85 | 60 | 56 |
| Galium aparine | 70 | 80 | 77 | 70 | 83 | 50 | 88 | 100 | 100 |
| Stellaria media | 78 | 98 | 76 | 80 | 100 | 85 | 87 | 100 | 100 |

| Active ingredient | I+VI+XVI | | | I+VII+XI | | | I+VII+XII | | |
|---|---|---|---|---|---|---|---|---|---|
| Triticum aestivum | 0 | 0 | 0 | 0 | 10 | 0 | 0 | 10 | 0 |
| Hordeum vulgare | 0 | 0 | 0 | 0 | 10 | 0 | 0 | 10 | 0 |
| Secale cereale | 0 | 0 | 0 | 0 | 20 | 0 | 0 | 20 | 0 |
| Avena fatua | 85 | 59 | 48 | 86 | 50 | 50 | 85 | 51 | 50 |
| Galium aparine | 83 | 95 | 100 | 80 | 100 | 100 | 75 | 100 | 100 |
| Stellaria media | 77 | 100 | 85 | 97 | 100 | 100 | 92 | 100 | 100 |

| Active ingredient | I+VII+XIII | | | I+VII+XIV | | | I+VII+XV | | |
|---|---|---|---|---|---|---|---|---|---|
| Triticum aestivum | 0 | 10 | 0 | 0 | 10 | 0 | 0 | 10 | 5 |
| Hordeum vulgare | 0 | 10 | 0 | 0 | 10 | 0 | 0 | 10 | 7 |
| Secale cereale | 0 | 20 | 0 | 0 | 20 | 0 | 0 | 20 | 10 |
| Avena fatua | 86 | 50 | 49 | 85 | 50 | 49 | 86 | 51 | 54 |
| Galium aparine | 72 | 100 | 75 | 72 | 100 | 75 | 87 | 100 | 100 |
| Stellaria media | 83 | 100 | 82 | 87 | 100 | 90 | 92 | 100 | 100 |

| Active ingredient | I+VII+XVI | | | I+VIII+XI | | | I+VIII+XII | | |
|---|---|---|---|---|---|---|---|---|---|
| Triticum aestivum | 0 | 10 | 0 | 0 | 0 | 0 | 0 | 0 | 0 |
| Hordeum vulgare | 0 | 10 | 0 | 0 | 0 | 0 | 0 | 0 | 0 |
| Secale cereale | 0 | 20 | 0 | 0 | 0 | 0 | 0 | 0 | 0 |
| Avena fatua | 85 | 52 | 50 | 85 | 48 | 49 | 84 | 50 | 49 |
| Galium aparine | 82 | 100 | 100 | 85 | 100 | 100 | 80 | 100 | 100 |
| Stellaria media | 83 | 100 | 90 | 87 | 100 | 100 | 82 | 100 | 100 |

| Active ingredient | I+VIII+XIII | | | I+VIII+XIV | | | I+VIII+XV | | |
|---|---|---|---|---|---|---|---|---|---|
| Triticum aestivum | 0 | 0 | 0 | 0 | 0 | 0 | 0 | 0 | 5 |
| Hordeum vulgare | 0 | 0 | 0 | 0 | 0 | 0 | 0 | 0 | 7 |
| Secale cereale | 0 | 0 | 0 | 0 | 0 | 0 | 0 | 0 | 10 |
| Avena fatua | 85 | 50 | 51 | 86 | 49 | 51 | 85 | 50 | 54 |
| Galium aparine | 75 | 95 | 80 | 75 | 95 | 80 | 90 | 100 | 100 |
| Stellaria media | 72 | 96 | 71 | 77 | 100 | 75 | 82 | 100 | 100 |

| Active ingredient | I+VIII+XVI | | | I+IX+XI | | | I+IX+XII | | |
|---|---|---|---|---|---|---|---|---|---|
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 83 | 50 | 52 | 85 | 51 | 50 | 84 | 51 | 50 |
| Galium aparine | 85 | 100 | 100 | 90 | 100 | 100 | 92 | 100 | 100 |
| Stellaria media | 72 | 98 | 82 | 92 | 100 | 100 | 96 | 100 | 100 |

| Active ingredient | I+IX+XIII | | | I+IX+XIV | | | I+IX+XV | | |
|---|---|---|---|---|---|---|---|---|---|
| Triticum aestivum | 0 | 0 | 0 | 0 | 0 | 0 | 0 | 0 | 5 |
| Hordeum vulgare | 0 | 0 | 0 | 0 | 0 | 0 | 0 | 0 | 7 |
| Secale cereale | 0 | 0 | 0 | 0 | 0 | 0 | 0 | 0 | 10 |
| Avena fatua | 86 | 49 | 50 | 84 | 48 | 49 | 84 | 50 | 54 |
| Galium aparine | 80 | 100 | 90 | 80 | 100 | 87 | 100 | 100 | 100 |
| Stellaria media | 80 | 100 | 80 | 85 | 100 | 86 | 100 | 100 | 100 |

| Active ingredient | I+IX+XVI | | | I+X+XI | | | I+X+XII | | |
|---|---|---|---|---|---|---|---|---|---|
| Triticum aestivum | 0 | 0 | 0 | 0 | 10 | 0 | 0 | 10 | 0 |
| Hordeum vulgare | 0 | 0 | 0 | 0 | 5 | 0 | 0 | 5 | 0 |
| Secale cereale | 0 | 0 | 0 | 0 | 8 | 0 | 0 | 8 | 0 |
| Avena fatua | 80 | 50 | 52 | 78 | 53 | 55 | 85 | 56 | 54 |
| Galium aparine | 95 | 100 | 100 | 75 | 100 | 100 | 76 | 94 | 98 |
| Stellaria media | 80 | 100 | 86 | 87 | 100 | 100 | 80 | 100 | 100 |

| Active ingredient | I+X+XIII | | | I+X+XIV | | | I+X+XV | | |
|---|---|---|---|---|---|---|---|---|---|
| Triticum aestivum | 0 | 10 | 0 | 0 | 10 | 0 | 0 | 10 | 5 |
| Hordeum vulgare | 0 | 5 | 0 | 0 | 5 | 0 | 0 | 7 | 7 |
| Secale cereale | 0 | 8 | 0 | 0 | 8 | 0 | 0 | 10 | 10 |
| Avena fatua | 82 | 50 | 48 | 78 | 52 | 50 | 84 | 54 | 60 |
| Galium aparine | 70 | 90 | 68 | 65 | 93 | 77 | 83 | 100 | 100 |
| Stellaria media | 75 | 90 | 76 | 80 | 100 | 82 | 85 | 100 | 100 |

| Active ingredient | I+X+XVI | | | I+XVI+XI | | | I+XVI+XII | | |
|---|---|---|---|---|---|---|---|---|---|
| Triticum aestivum | 0 | 10 | 0 | 0 | 0 | 0 | 0 | 0 | 0 |
| Hordeum vulgare | 0 | 5 | 0 | 0 | 0 | 0 | 0 | 0 | 0 |
| Secale cereale | 0 | 8 | 0 | 0 | 0 | 0 | 0 | 0 | 0 |
| Avena fatua | 80 | 49 | 48 | 83 | 54 | 60 | 88 | 52 | 60 |
| Galium aparine | 78 | 94 | 100 | 80 | 100 | 100 | 82 | 100 | 100 |
| Stellaria media | 76 | 98 | 80 | 75 | 97 | 100 | 75 | 80 | 100 |

| Active ingredient | I+XVI+XIII | | | I+XVI+XIV | | | I+XIII+XI | | |
|---|---|---|---|---|---|---|---|---|---|
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 77 | 48 | 47 | 76 | 50 | 48 | 85 | 47 | 52 |

-continued

| | | | | | | | | | |
|---|---|---|---|---|---|---|---|---|---|
| Galium aparine | 74 | 100 | 75 | 74 | 97 | 76 | 78 | 70 | 98 |
| Stellaria media | 65 | 75 | 63 | 70 | 75 | 70 | 80 | 74 | 95 |

| Active ingredient | I+XIII+XIV | | | I+II+XVII | | | I+III+XVII | | |
|---|---|---|---|---|---|---|---|---|---|
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 78 | 50 | 48 | 80 | 47 | 50 | 79 | 50 | 48 |
| Galium aparine | 64 | 80 | 66 | 75 | 100 | 74 | 75 | 100 | 76 |
| Stellaria media | 68 | 75 | 69 | 80 | 100 | 75 | 68 | 98 | 68 |

| Active ingredient | I+IV+XVII | | | I+V+XVII | | | I+VI+XVII | | |
|---|---|---|---|---|---|---|---|---|---|
| Triticum aestivum | 0 | 0 | 0 | 0 | | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 80 | 52 | 49 | 80 | 51 | 50 | 85 | 68 | 55 |
| Galium aparine | 80 | 100 | 80 | 82 | 100 | 80 | 78 | 90 | 72 |
| Stellaria media | 75 | 100 | 77 | 70 | 100 | 70 | 75 | 100 | 74 |

| Active ingredient | I+VII+XVII | | | I+VIII+XVII | | | I+IX+XVII | | |
|---|---|---|---|---|---|---|---|---|---|
| Triticum aestivum | 0 | 10 | 0 | 0 | 0 | 0 | 0 | 0 | 0 |
| Hordeum vulgare | 0 | 10 | 0 | 0 | 0 | 0 | 0 | 0 | 0 |
| Secale cereale | 0 | 20 | 0 | 0 | 0 | 0 | 0 | 0 | 0 |
| Avena fatua | 76 | 50 | 48 | 78 | 47 | 51 | 80 | 50 | 48 |
| Galium aparine | 72 | 100 | 70 | 77 | 98 | 76 | 87 | 100 | 90 |
| Stellaria media | 80 | 100 | 79 | 70 | 95 | 70 | 80 | 100 | 82 |

| Active ingredient | I+X+XVII | | |
|---|---|---|---|
| Triticum aestivum | 0 | 10 | 0 |
| Hordeum vulgare | 0 | 5 | 0 |
| Secale cereale | 0 | 8 | 0 |
| Avena fatua | 78 | 52 | 50 |
| Galium aparine | 65 | 100 | 70 |
| Stellaria media | 74 | 100 | 72 |

0 = no damage
100 = complete destruction

EXAMPLE 5

In the greenhouse, various plants were treated at a growth height of from 2 to 24 cm with the following amounts of the following individual active ingredients and compositions thereof as tankmix emulsions or solutions:

I. ethyl-N-benzoyl-N-(3,4-dichlorophenyl)-2-amino-propionate, 0.5 and 1.5 kg/ha;
II. 3-isopropyl-2,1,3-benzothiadiazinone-(4)-2,2-dioxide, 0.5 and 1.5 kg/ha;
III. 3-isopropyl-2,1,3-benzothiadiazinone-(4)-2,2-dioxide, sodium salt, 0.5 and 1.5 kg/ha;
IV. 3-isopropyl-2,1,3-benzothiadiazinone-(4)-2,2-dioxide, dimethylamine salt, 0.5 and 1.5 kg/ha;
V. 3-isopropyl-2,1,3-benzothiadiazinone-(4)-2,2-dioxide, diethanolamine salt, 0.5 and 1.5 kg/ha;
XI. α-(2-methyl-4-chlorophenoxy)-propionic acid, dimethylamine salt, 0.25 and 1.5 kg/ha;
XII. α-(2,4-dichlorophenoxy)-propionic acid, dimethylamine salt, 0.25 and 1.5 kg/ha;
XIII. 2,4-dichlorophenoxyacetic acid, dimethylamine salt, 0.25 and 1.5 kg/ha;
XIV. 2-methyl-4-chlorophenoxyacetic acid, dimethylamine salt, 0.25 and 1.5 kg/ha;
XV. α-(2,4,5-trichlorophenoxy)-propionic acid, dimethylamine salt, 0.25 and 1.5 kg/ha;
XVI. 2,4,5-trichlorophenoxyacetic acid, potassium salt, 0.25 and 1.5 kg/ha;
XVII. γ-(2,4-dichlorophenoxy)-butyric acid, dimethylamine salt, 0.25 and 1.5 kg/ha;

I+II+XII+XVI  I+III+XII+XVI  I+IV+XII+XVI  I+V+XII+XVI  I+II+XIV+XVI
I+III+XIV+XVI  I+IV+XIV+XVI  I+V+XIV+XVI  I+II+XIII+XVI
I+III+XIII+XVI  I+IV+XIII+XVI  I+V+XIII+XVI  I+II+XI+XVI  I+III+XI+XVI
I+IV+XI+XVI  I+V+XI+XVI  I+II+XIII+XI  I+III+XIII+XI  I+IV+XIII+XI
I+V+XIII+XI  I+II+XIII+XIV  I+III+XIII+XIV
I+IV+XIII+XIV  I+V+XIII+XIV each of these compositions at a rate of 0.5+0.25+0.25+0.25 kg/ha. After 12 to 15 days it was ascertained that the compositions had a better herbicidal action than their components, combined with the same good crop plant compatibility.

The results are given below:

| Active ingredient kg/ha | I | | II | | III | | IV | | V | |
|---|---|---|---|---|---|---|---|---|---|---|
| | 0.5 | 1.5 | 0.5 | 1.5 | 0.5 | 1.5 | 0.5 | 1.5 | 0.5 | 1.5 |
| Triticum aestivum | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 |
| Secale cereale | 0 | 0 | 0 | 0 | 0 | 0 | 0 | 0 | 0 | 0 |
| Avena fatua | 26 | 60 | 0 | 0 | 0 | 0 | 0 | 0 | 0 | 0 |
| Galium aparine | 0 | 14 | 35 | 75 | 30 | 75 | 30 | 60 | 35 | 80 |
| Stellaria media | 7 | 15 | 30 | 70 | 20 | 70 | 20 | 70 | 20 | 85 |

| Active ingredient | XI | | XII | | XIII | | XIV | | XVI | |
|---|---|---|---|---|---|---|---|---|---|---|
| Triticum aestivum | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 5 |
| Secale cereale | 0 | 0 | 0 | 0 | 0 | 0 | 0 | 0 | 0 | 7 |
| Avena fatua | 0 | 0 | 0 | 5 | 0 | 0 | 0 | 0 | 0 | 0 |

| | | | | | | | | | | |
|---|---|---|---|---|---|---|---|---|---|---|
| Galium aparine | 15 | 70 | 10 | 75 | 5 | 25 | 5 | 25 | 15 | 80 |
| Stellaria media | 20 | 70 | 15 | 75 | 3 | 20 | 10 | 35 | 5 | 36 |

| Active ingredient kg/ha | I+II+XII+XVI 0.5+0.5+0.25+0.25 | I+III+XII+XVI 0.5+0.5+0.25+0.25 | I+IV+XII+XVI 0.5+0.5+0.25+0.25 |
|---|---|---|---|
| Triticum aestivum | 0 | 0 | 0 |
| Hordeum vulgare | 0 | 0 | 0 |
| Secale cereale | 0 | 0 | 0 |
| Avena fatua | 74 | 72 | 70 |
| Galium aparine | 100 | 100 | 100 |
| Stellaria media | 100 | 93 | 94 |

| Active ingredient | I+V+XII+XVI | I+II+XIV+XVI | I+III+XIV+XVI |
|---|---|---|---|
| Triticum aestivum | 0 | 0 | 0 |
| Hordeum vulgare | 0 | 0 | 0 |
| Secale cereale | 0 | 0 | 0 |
| Avena fatua | 69 | 64 | 65 |
| Galium aparine | 100 | 90 | 90 |
| Stellaria media | 93 | 88 | 80 |

| Active ingredient | I+IV+XIV+XVI | I+V+XIV+XVI | I+II+XIII+XVI |
|---|---|---|---|
| Triticum aestivum | 0 | 0 | 0 |
| Hordeum vulgare | 0 | 0 | 0 |
| Secale cereale | 0 | 0 | 0 |
| Avena fatua | 62 | 60 | 60 |
| Galium aparine | 89 | 92 | 90 |
| Stellaria media | 78 | 80 | 80 |

| Active ingredient | I+III+XIII+XVI | I+IV+XIII+XVI | I+V+XIII+XVI |
|---|---|---|---|
| Triticum aestivum | 0 | 0 | 0 |
| Hordeum vulgare | 0 | 0 | 0 |
| Secale cereale | 0 | 0 | 0 |
| Avena fatua | 62 | 65 | 64 |
| Galium aparine | 87 | 90 | 92 |
| Stellaria media | 77 | 80 | 79 |

| Active ingredient | I+II+XI+XVI | I+III+XI+XVI | I+IV+XI+XVI |
|---|---|---|---|
| Triticum aestivum | 0 | 0 | 0 |
| Hordeum vulgare | 0 | 0 | 0 |
| Secale cereale | 0 | 0 | 0 |
| Avena fatua | 70 | 69 | 68 |
| Galium aparine | 100 | 100 | 100 |
| Stellaria media | 98 | 96 | 95 |

| Active ingredient | I+V+XI+XVI | I+II+XIII+XI | I+III+XIII+XI |
|---|---|---|---|
| Triticum aestivum | 0 | 0 | 0 |
| Hordeum vulgare | 0 | 0 | 0 |
| Secale cereale | 0 | 0 | 0 |
| Avena fatua | 68 | 66 | 65 |
| Galium aparine | 100 | 95 | 90 |
| Stellaria media | 93 | 98 | 94 |

| Active ingredient | I+IV+XIII+XI | I+V+XIII+XI | I+II+XIII+XIV |
|---|---|---|---|
| Triticum aestivum | 0 | 0 | 0 |
| Hordeum vulgare | 0 | 0 | 0 |
| Secale cereale | 0 | 0 | 0 |
| Avena fatua | 64 | 65 | 62 |
| Galium aparine | 92 | 97 | 82 |
| Stellaria media | 90 | 95 | 87 |

| Active ingredient | I+III+XIII+XIV | I+IV+XIII+XIV | I+V+XIII+XIV |
|---|---|---|---|
| Triticum aestivum | 0 | 0 | 0 |
| Hordeum vulgare | 0 | 0 | 0 |
| Secale cereale | 0 | 0 | 0 |
| Avena fatua | 60 | 60 | 63 |
| Galium aparine | 78 | 80 | 83 |
| Stellaria media | 80 | 77 | 84 |

0 = no damage
100 = complete destruction

EXAMPLE 6

In the greenhouse, various plants were treated at a growth height of from 2 to 24 cm with the following amounts of the following individual active ingredients and compositions thereof as emulsions and solutions:

I. ethyl-N-benzoyl-N-(3,4-dichlorophenyl)-2-amino-propionate, 0.5, 0.75, 1 and 1.5 kg/ha;

VI. 2-sec-butyl-4,6-dinitrophenyl acetate, 0.5, 0.75, 1 and 1.5 kg/ha;

VII. 3,5-diiodo-4-hydroxybenzonitrile, lithium salt, 0.5, 0.75, 1 and 1.5 kg/ha;

VIII. 3,5-dibromo-4-hydroxybenzaldoxime-O-(2′,4′-dinitrophenyl)-ether, sodium salt, 0.5, 0.75, 1 and 1.5 kg/ha;

IX. 3,5-dibromo-4-hydroxybenzaldoxime-O-(2′-cyano-4′-nitrophenyl)-ether, sodium salt, 0.5, 0.75, 1 and 1.5 kg/ha;

X. 3,5-dibromo-4-hydroxybenzonitrile, sodium salt, 0.5, 0.75, 1 and 1.5 kg/ha;

XI. α-(2-methyl-4-chlorophenoxy)-propionic acid, dimethylamine salt, 0.5, 0.75, 1 and 1.5 kg/ha;
XII. α-(2,4-dichlorophenoxy)-propionic acid, dimethylamine salt, 0.5, 0.75, 1 and 1.5 kg/ha;
XIII. 2,4-dichlorophenoxyacetic acid, dimethylamine salt, 0.5, 0.75, 1 and 1.5 kg/ha;
XIV. 2-methyl-4-chlorophenoxyacetic acid, dimethylamine salt, 0.5, 0.75, 1 and 1.5 kg/ha;
XV. α(2,4,5-trichlorophenoxy)-propionic acid, dimethylamine salt, 0.5, 0.75, 1 and 1.5 kg/ha;
XVI. 2,4,5-trichlorophenoxyacetic acid, potassium salt, 0.5, 0.75, 1 and 1.5 kg/ha;
XVII. γ-(2,4-dichlorophenoxy)-butyric acid, dimethylamine salt, 0.5, 0.75, 1 and 1.5 kg/ha;

I+VI:      0.5+1, 1+0.5   and 0.75 + 0.75 kg/ha;
I+VII:     ″                ″
I+VIII:    ″                ″
I+IX:      ″                ″
I+X:       ″                ″
I+XI:      ″                ″
I+XII:     ″                ″
I+XIII:    ″                ″
I+XIV:     ″                ″
I+XV:      ″                ″
I+XVI:     ″                ″
I+XVII:    ″                ″

After 12 to 15 days it was ascertained that the compositions had a better herbicidal action than their components, combined with the same good crop plant compatibility.

The results are given below:

| Active ingredient kg/ha | VI | | | | VII | | | | VIII | | | |
|---|---|---|---|---|---|---|---|---|---|---|---|---|
| | 0.5 | 1 | 0.75 | 1.5 | 0.5 | 1 | 0.75 | 1.5 | 0.5 | 1 | 0.75 | 1.5 |
| Triticum aestivum | 0 | 0 | 0 | 0 | 0 | 10 | 0 | 20 | 0 | 0 | 0 | 10 |
| Hordeum vulgare | 0 | 0 | 0 | 0 | 0 | 10 | 0 | 10 | 0 | 0 | 0 | 15 |
| Secale cereale | 0 | 0 | 0 | 5 | 0 | 20 | 0 | 20 | 0 | 0 | 0 | 10 |
| Avena fatua | 0 | 12 | 10 | 15 | 0 | 0 | 0 | 0 | 0 | 0 | 0 | 0 |
| Galium aparine | 30 | 46 | 40 | 50 | 30 | 60 | 56 | 70 | 30 | 50 | 45 | 60 |
| Stellaria media | 40 | 60 | 50 | 75 | 30 | 55 | 48 | 80 | 30 | 48 | 35 | 70 |

| Active ingredient | IX | | | | X | | | | XI | | | |
|---|---|---|---|---|---|---|---|---|---|---|---|---|
| Triticum aestivum | 0 | 0 | 0 | 0 | 5 | 10 | 7 | 12 | 0 | 0 | 0 | 0 |
| Hordeum vulgare | 0 | 0 | 0 | 0 | 0 | 5 | 0 | 6 | 0 | 0 | 0 | 0 |
| Secale cereale | 0 | 0 | 0 | 0 | 0 | 8 | 0 | 10 | 0 | 0 | 0 | 0 |
| Avena fatua | 0 | 0 | 0 | 0 | 0 | 0 | 0 | 0 | 0 | 0 | 0 | 0 |
| Galium fatua | 30 | 90 | 45 | 100 | 20 | 50 | 40 | 67 | 30 | 50 | 45 | 70 |
| Stellaria media | 30 | 80 | 35 | 100 | 25 | 70 | 54 | 78 | 30 | 45 | 40 | 70 |

| Active ingredient | XII | | | | XIII | | | | XIV | | | |
|---|---|---|---|---|---|---|---|---|---|---|---|---|
| Triticum aestivum | 0 | 0 | 0 | 0 | 0 | 0 | 0 | 0 | 0 | 0 | 0 | 0 |
| Hordeum vulgare | 0 | 0 | 0 | 0 | 0 | 0 | 0 | 0 | 0 | 0 | 0 | 0 |
| Secale cereale | 0 | 0 | 0 | 0 | 0 | 0 | 0 | 0 | 0 | 0 | 0 | 0 |
| Avena fatua | 0 | 0 | 0 | 5 | 0 | 0 | 0 | 0 | 0 | 0 | 0 | 0 |
| Galium aparine | 50 | 65 | 58 | 75 | 10 | 20 | 15 | 25 | 10 | 20 | 15 | 25 |
| Stellaria media | 25 | 55 | 40 | 75 | 5 | 10 | 8 | 20 | 15 | 20 | 18 | 35 |

| Active ingredient | XV | | | | XVI | | | | I | | | |
|---|---|---|---|---|---|---|---|---|---|---|---|---|
| Triticum aestivum | 0 | 5 | 0 | 10 | 0 | 0 | 0 | 0 | 0 | 0 | 0 | 0 |
| Hordeum vulgare | 0 | 7 | 0 | 10 | 0 | 0 | 0 | 5 | 0 | 0 | 0 | 0 |
| Secale cereale | 0 | 10 | 0 | 12 | 0 | 0 | 0 | 7 | 0 | 0 | 0 | 0 |
| Avena fatua | 0 | 4 | 0 | 10 | 0 | 0 | 0 | 0 | 25 | 45 | 37 | 60 |
| Galium aparine | 40 | 60 | 48 | 85 | 30 | 60 | 45 | 80 | 0 | 10 | 6 | 14 |
| Stellaria media | 30 | 65 | 50 | 85 | 10 | 20 | 16 | 36 | 7 | 12 | 10 | 15 |

| Active ingredient | XVII | | | |
|---|---|---|---|---|
| Triticum aestivum | 0 | 0 | 0 | 0 |
| Hordeum vulgare | 0 | 0 | 0 | 0 |
| Secale cereale | 0 | 0 | 0 | 0 |
| Avena fatua | 0 | 0 | 0 | 0 |
| Galium aparine | 12 | 18 | 15 | 25 |
| Stellaria media | 5 | 8 | 6 | 15 |

0 = no damage
100 = complete destruction

| Active ingredient kg/ha | I+VI | | | I+VII | | | I+VIII | | |
|---|---|---|---|---|---|---|---|---|---|
| | 0.5+1 | 1+0.5 | 0.75+0.75 | 0.5+1 | 1+0.5 | 0.75+0.75 | 0.5+1 | 1+0.5 | 0.75+0.75 |
| Triticum aestivum | 0 | 0 | 0 | 10 | 0 | 0 | 0 | 0 | 0 |
| Hordeum vulgare | 0 | 0 | 0 | 10 | 0 | 0 | 0 | 0 | 0 |
| Secale cereale | 0 | 0 | 0 | 20 | 0 | 0 | 0 | 0 | 0 |
| Avena fatua | 75 | 85 | 89 | 64 | 84 | 77 | 65 | 86 | 75 |
| Galium aparine | 80 | 80 | 92 | 100 | 79 | 100 | 90 | 80 | 91 |
| Stellaria media | 100 | 92 | 100 | 100 | 82 | 98 | 94 | 81 | 85 |

| Active ingredient | I+IX | | | I+X | | | I+XI | | |
|---|---|---|---|---|---|---|---|---|---|
| Triticum aestivum | 0 | 0 | 0 | 10 | 5 | 7 | 0 | 0 | 0 |
| Hordeum vulgare | 0 | 0 | 0 | 5 | 0 | 0 | 0 | 0 | 0 |
| Secale cereale | 0 | 0 | 0 | 8 | 0 | 0 | 0 | 0 | 0 |
| Avena fatua | 63 | 83 | 74 | 66 | 87 | 76 | 64 | 85 | 77 |
| Galium aparine | 100 | 82 | 90 | 89 | 70 | 86 | 90 | 80 | 91 |
| Stellaria media | 100 | 84 | 87 | 100 | 80 | 100 | 92 | 83 | 90 |

-continued

| Active ingredient | I+XII | | | I+XIII | | | I+XIV | | |
|---|---|---|---|---|---|---|---|---|---|
| Triticum aestivum | 0 | 0 | 0 | 0 | 0 | 0 | 0 | 0 | 0 |
| Hordeum vulgare | 0 | 0 | 0 | 0 | 0 | 0 | 0 | 0 | 0 |
| Secale cereale | 0 | 0 | 0 | 0 | 0 | 0 | 0 | 0 | 0 |
| Avena fatua | 65 | 83 | 75 | 65 | 84 | 78 | 66 | 85 | 76 |
| Galium aparine | 100 | 100 | 100 | 60 | 61 | 62 | 61 | 60 | 61 |
| Stellaria media | 100 | 77 | 90 | 58 | 57 | 58 | 67 | 69 | 68 |

| Active ingredient | I+XV | | | I+XVI | | | I+XVIII | | |
|---|---|---|---|---|---|---|---|---|---|
| Triticum aestivum | 5 | 0 | 0 | 0 | 0 | 0 | 0 | 0 | 0 |
| Hordeum vulgare | 7 | 0 | 0 | 0 | 0 | 0 | 0 | 0 | 0 |
| Secale cereale | 10 | 0 | 0 | 0 | 0 | 0 | 0 | 0 | 0 |
| Avena fatua | 69 | 86 | 77 | 64 | 85 | 75 | 65 | 83 | 73 |
| Galium aparine | 98 | 90 | 94 | 100 | 80 | 92 | 59 | 62 | 61 |
| Stellaria media | 100 | 82 | 100 | 68 | 64 | 66 | 55 | 57 | 56 |

0 = no damage
100 = complete destruction

I claim:

1. A herbicide composition comprising an inert carrier having dispersed therein a herbicidally effective amount of a mixture of
    a. a compound of the formula

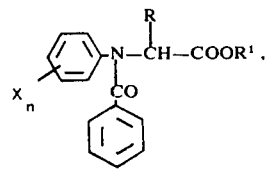

wherein X denotes chloro, R denotes hydrogen or lower alkyl, R¹ denotes lower alkyl and n denotes 0, 1, 2 or 3, and
    b. a compound of the formula

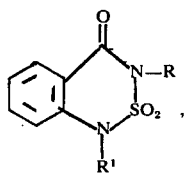

wherein R denotes lower alkyl and R¹ denotes hydrogen, or the ammonium, potassium, sodium, lithium, calcium, magnesium, ethylamine, dimethylamine, diethylamine, diethanolamine, ethanolamine, dimethylethanolamine, or trimethylamine salt of said compound in a weight ratio of $a$ to $b$ in the range of 2:1 to 1:2.

2. A herbicide composition as claimed in claim 1 wherein compound a is ethyl-N-benzoyl-N-(3,4-dichlorophenyl)-2-aminopropionate.

3. A herbicide composition as claimed in claim 1 wherein compound a is ethyl-N-benzoyl-N-(3,4-dichlorophenyl)-2-aminopropionate and compound b is 3-isopropyl-2,1,3-benzothiadiazinone-(4)-2,2-dioxide or the sodium, dimethylamine or diethanolamine salt thereof.

* * * * *